(12) United States Patent
Seddon et al.

(10) Patent No.: US 7,928,031 B2
(45) Date of Patent: Apr. 19, 2011

(54) CATALYST COMPRISING INDIUM SALT AND ORGANIC IONIC LIQUID AND PROCESS FOR FRIEDEL-CRAFTS REACTIONS

(75) Inventors: Kenneth Richard Seddon, Donaghadee (GB); Christopher Hardacre, Belfast (GB); Barry Joseph McAuley, Greenisland (GB)

(73) Assignee: The Queen's University of Belfast, Belfast (GB)

( * ) Notice: Subject to any disclaimer, the term of this patent is extended or adjusted under 35 U.S.C. 154(b) by 1145 days.

(21) Appl. No.: 10/491,453

(22) PCT Filed: Oct. 2, 2002

(86) PCT No.: PCT/GB02/04454
§ 371 (c)(1),
(2), (4) Date: Nov. 5, 2004

(87) PCT Pub. No.: WO03/028883
PCT Pub. Date: Apr. 10, 2003

(65) Prior Publication Data
US 2005/0054694 A1      Mar. 10, 2005

(30) Foreign Application Priority Data
Oct. 2, 2001   (GB) .................................. 0123597.7

(51) Int. Cl.
*B01J 31/26*     (2006.01)
*A01N 43/82*     (2006.01)
*C07D 237/02*    (2006.01)
*C07D 239/02*    (2006.01)

(52) U.S. Cl. ......... 502/169; 514/362; 544/224; 544/242
(58) Field of Classification Search .................. 514/362; 502/169; 544/224, 242
See application file for complete search history.

(56) References Cited

U.S. PATENT DOCUMENTS

| 4,895,984 | A | | 1/1990 | Eggersdorfer et al. | |
| 5,552,241 | A | * | 9/1996 | Mamantov et al. | 429/103 |
| 5,731,101 | A | | 3/1998 | Sherif et al. | |
| 5,824,832 | A | * | 10/1998 | Sherif et al. | 585/455 |
| 6,368,486 | B1 | * | 4/2002 | Thompson et al. | 205/406 |

FOREIGN PATENT DOCUMENTS

| DE | 101 08 893 A1 | 10/2002 |
| JP | 9-262479 A | 10/1997 |
| WO | WO 98/03454 A1 | 1/1998 |
| WO | WO 00/37400 | 6/2000 |
| WO | WO 01/32308 A1 | 5/2001 |
| WO | WO 02/072519 A2 | 9/2002 |

OTHER PUBLICATIONS

Boon et al., *Friedel-Crafts Reactions in Ambient-Temperature Molten Salts*, J. Org. Chem. (1986) vol. 51, No. 4, pp. 480-483.

(Continued)

*Primary Examiner* — Glenn Caldarola
*Assistant Examiner* — Jim Goloboy
(74) *Attorney, Agent, or Firm* — Hodgson Russ LLP

(57) ABSTRACT

Disclosed is a catalyst composition based on an indium salt and an organic ionic liquid, a process for making the catalyst composition, and uses thereof. The catalyst composition is particularly suitable for Lewis acid catalysed electrophilic aromatic substitution reactions, such as Friedel-Crafts alkylation reactions an Friedel-Crafts acylation reactions.

37 Claims, 1 Drawing Sheet

OTHER PUBLICATIONS

Figure 1:
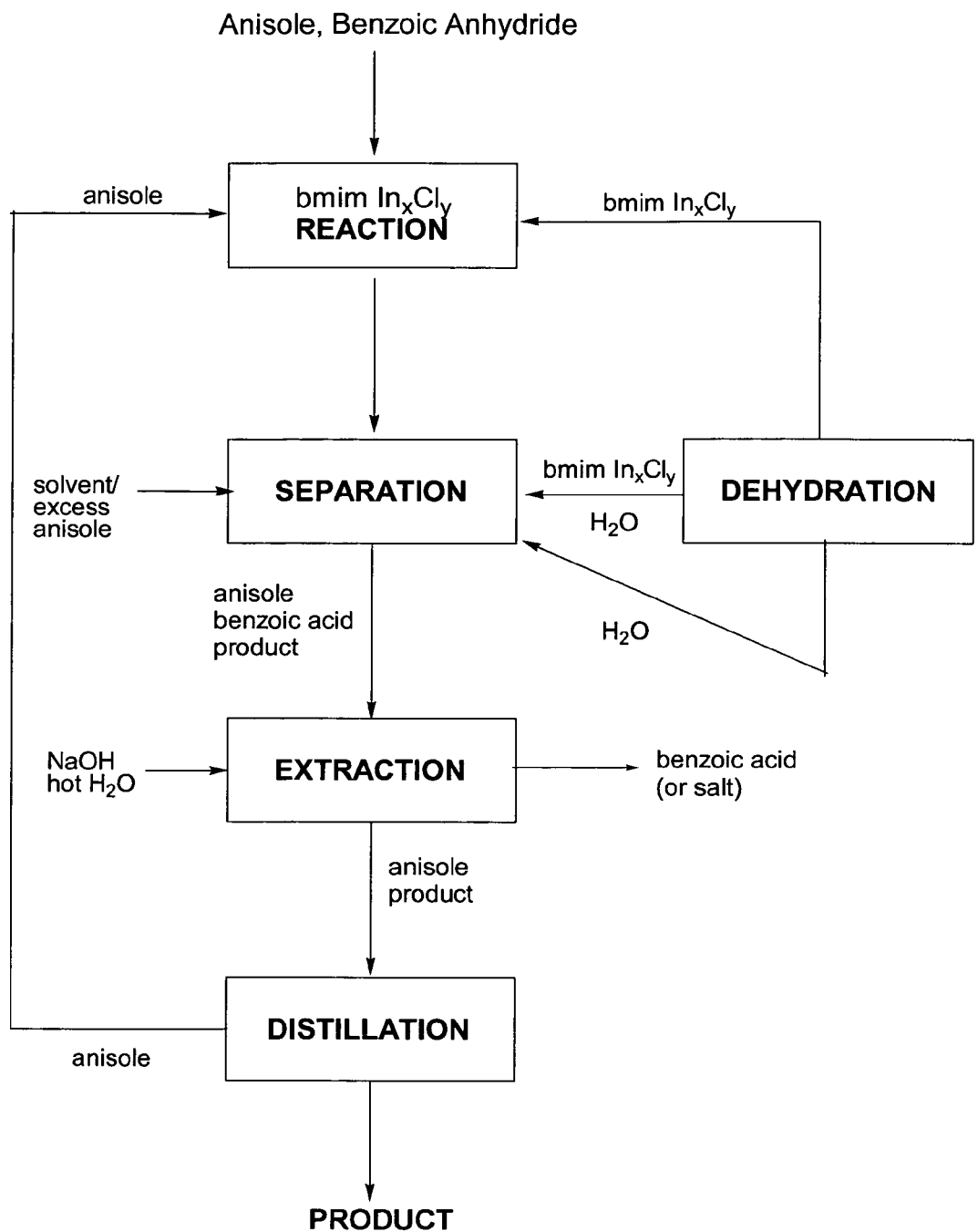

Harada et al., *The Catalytic Friedel-Crafts Acylation Reaction and the Catalytic Beckmann Rearrangement Promoted by a Gallium(III) or an Antimony(V) Cationic Species*, Synthesis (Dec. 1991) pp. 1216-1220.

Lee et al., *Lantanide Triflate-Catalyzed Three Component Synthesis of Alpha-Amino Phosphonates in Ionic Liquids. A Catalyst Reactivity and Reusability Study*, Chem. Comm. (2001) vol. 17, pp. 1698-1699.

Tian et al., *Studies on Room Temperature Ionic Liquid Containing Rarely Scattered Metals. The System of InCl3/BPC*, Database Accession No. 2002:841252 (XP-002226272).

Wasserscheid et al., *Ionic Liquids—New "Solutions" for Transition Metal Catalysis*, Agnew. Chem. Int. Ed. (2000) vol. 39, No. 21, pp. 3772-3789.

\* cited by examiner

CATALYST COMPRISING INDIUM SALT AND ORGANIC IONIC LIQUID AND PROCESS FOR FRIEDEL-CRAFTS REACTIONS

The present invention relates to electrophilic aromatic substitution reactions. In particular, the present invention is concerned with Lewis acid catalysed electrophilic aromatic substitution reactions, such as Friedel-Crafts alkylation reactions and Friedel-Crafts acylation reactions.

The present invention is particularly concerned with Lewis acid catalysed electrophilic aromatic substitution reactions comprising the use of an ionic liquid and an indium(III) halide. The ionic liquid and indium(III) halide components together form the "ionic liquid catalyst system" of the present invention.

Friedel-Crafts reactions generally involve the alkylation or acylation of an aromatic compound by an electrophilic reagent. In a Friedel-Crafts alkylation reaction, a compound containing an aromatic ring, Ar is reacted with an alkylating agent in the presence of a Lewis acid catalyst, typically $AlCl_3$ or $BF_3$, for example:

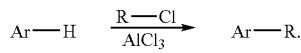

The alkylating agent is typically an alkyl halide, e.g. an alkyl chloride. However, other alkylating agents, such as olefins, alcohols, dienes, alkynes, ethers sulfonates and inorganic ester can be used (see Roberts, Khalaf: *Friedel-Crafts Alkylation Chemistry*, Marcel Dekker, New York, 1984 and Olah: Friedel-Crafts Chemistry, Wiley, New York, 1973).

In the Friedel-Crafts acylation reaction, an acylating agent is reacted with an aromatic group, in the presence of a Lewis acid catalyst, such as $AlCl_3$ to produce a ketone:

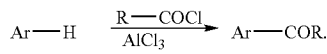

The acylating agent is typically an acyl halide, although acid anhydrides, carboxylic acids and ketenes can be used. The reaction can be used for the acylating of a wide range of aromatic substrates.

The Friedel-Crafts acylation reaction is one of the most important methods for the preparation of aryl ketones and is thus a reaction of considerable commercial and industrial importance.

However, there are several disadvantages associated with prior art Friedel-Crafts alkylation and acylation reactions. Typically, the reaction product is isolated by first quenching the reaction mixture with water. This destroys the aluminium chloride catalyst, and at the same time generates a large amount of aluminium-containing waste products that must be disposed of. The catalyst thus cannot be re-used or recycled.

Furthermore, in the Friedel-Crafts acylation process, the Lewis acid "catalyst" such as aluminium chloride or iron(III) chloride forms a stable adduct with the reaction product (ketone), and this means that the catalyst must be used in stoichiometric quantities. Since the reaction product can only be liberated by hydrolyzing the ketone-catalyst adduct, this leads to destruction of the Lewis-acid 'catalyst'. In other words, this process is not truly catalytic, nor is the system recyclable.

Thus, there are significant environmental problems in the use of aluminium. This in turn means that the Friedel-Crafts acylation and alkylation processes generate considerable amounts of waste, in terms of aluminium salts and hydrochloric acid. Further, the hydrolysis process generates a large amount of aqueous solutions and suspensions containing aluminium salts, which, if used on an industrial scale, requires additional treatment steps for eventual disposal, and which significantly adds to the cost of the operation.

WO 99/19288 discloses a Friedel-Crafts acylation reaction carried out in the presence of an ionic liquid system as catalyst. The ionic liquid system employed therein comprises as a Lewis acid, iron(III) chloride, and as a base, an ionic liquid [Q]Cl, wherein Q can be a range of organic cations such as substituted imidazolium, pyridinium, ammonium or phosphonium. The use of 1-ethyl-3-methylimidazolium chloride, [emim]Cl, is specifically disclosed.

According to WO 99/19288, iron(III) chloride and [emim]Cl, form the ionic liquid system denoted "[emim]Cl—$FeCl_3$". Friedel-Crafts acylation of benzene with acetyl chloride in the presence of this ionic liquid system produces acetophenone, which can be isolated by solvent extraction. According to the disclosure of WO 99/19288, the catalyst is deactivated in the process, and is not recovered. Further, it is stated that the product acetophenone deactivates the catalyst so that it the product must be continuously removed from the reaction vessel to free up the catalyst.

Therefore, it is desirable to develop Friedel-Crafts alkylation and acylation systems which are catalysed by species which can be used in truly catalytic amounts. Additionally, it is desirable to develop Friedel-Crafts acylation catalysts that do not form stable adducts with the ketone products, and thus allow the products of the reaction to be removed from the reaction mixture without destruction of the catalyst system, thus allowing the catalyst to be recycled.

It would be a further advantage to provide recyclable Friedel-Crafts catalyst systems that can be reused directly after isolation from the reaction mixture, i.e. with little or no additional purification steps. Furthermore, it is desirable that the recycled catalyst exhibits minimal loss of activity, that is, the recycled catalyst is not significantly deactivated, so that subsequent reactions employing the recycled catalyst proceeds with a percentage conversion of starting material (aromatic substrate) to product that is similar to the reaction with fresh catalyst (e.g. less than 25%, preferably less than 20% and even more preferably less than 15% loss of the initial percentage conversion).

Even more desirable would be a Friedel-Crafts catalyst system that can be repeatedly recycled (e.g. more than two runs of recycled catalyst, preferably more than three runs of recycled catalyst, even more preferably at least five runs of recycled catalyst). If would be particularly advantageous to provide such Friedel-Crafts catalyst systems that can be repeated recycled with minimal loss of catalyst activity.

The present invention provides a catalyst system and Friedel-Crafts processes that overcomes one or more of the problems associated with prior art Friedel-Crafts systems.

According to a first aspect of the present invention, there is provided a catalyst composition formed by combining an organic ionic liquid with an indium(III) halide.

The catalyst composition of the present invention thus comprises in admixture (a) an organic ionic liquid and (b) an indium(III) halide. Although the actual identity of the catalytic species is not known with certainty, it is believed that the catalyst composition comprises ionic species resulting from reaction between the organic ionic liquid and indium chloride.

The catalyst composition of the present invention may thus be described as comprising a plurality of ionic species including:
(a) cationic species derived from an organic ionic liquid, and
(b) at least one species comprising indium,
and may additionally comprise halide ions.

According to an alternative definition of the present invention, the catalyst composition comprises a plurality of ionic species and being obtainable by mixing an organic ionic liquid and an indium(III) (preferably an indium(III) halide, and more preferably, indium(III) chloride).

The term "ionic liquid" refers to a liquid that is capable of being produced by melting a solid, and when so produced, consists solely of ions. Ionic liquids may be derived from organic salts, especially salts of heterocyclic nitrogen-containing compounds, and such ionic liquids are particularly preferred for use in the processes of the present invention. Ionic liquids may be regarded as consisting of two components, which are a positively charged cation and a negatively charged anion.

An ionic liquid may be formed from a homogeneous substance comprising one species of cation and one species of anion, or can be composed of more than one species of cation and/or anion. Thus, an ionic liquid may be composed of more than one species of cation and one species of anion. An ionic liquid may further be composed of one species of cation, and one or more species of anion.

Thus, in summary, the term "ionic liquid" as used herein may refer to a homogeneous composition consisting of a single salt (one cationic species and one anionic species) or it may refer to a heterogeneous composition containing more than one species of cation and/or more than one species of anion. For the purposes of the present invention, it is preferred that the anion species of the ionic liquid comprises a halide, i.e. $F^-$, $Cl^-$, $Br^-$ or $I^-$. Preferably, the ionic liquid employed in the present invention is composed of a single species of halide anions, with $Cl^-$ being particularly preferred.

The term "ionic liquid" includes compounds having both high melting temperature and compounds having low melting points, e.g. at or below room temperature (i.e. 15-30° C.). The latter are often referred to as "room temperature ionic liquids" and are often derived from organic salts having pyridinium and imidazolium-based cations.

A feature of ionic liquids is that they have particularly low (essentially zero) vapour pressures. Many organic ionic liquids have low melting points (e.g. less than 100° C., particularly less than 100° C., and around room temperature, e.g. 15-30° C. and some have melting points well below 0° C. For the purposes of the present invention, it is desirable that the organic ionic liquid has a melting point of 250° C. or less, preferably 150° C. or less, more preferably 100° C. or less and even more preferably 80° C. or less, although any compound that meets the criteria of being a salt (consisting of an anion and cation) and which is liquid at or near the reaction temperature, or exists in a fluid state during any stage of the reaction can be defined as an organic ionic liquid especially suitable for use in the process of the present invention.

Ionic liquids useful for preparing the catalyst composition of the present invention include those comprising an imidazolium, pyridinium, pyridazinium, pyrazinium, oxazolium, triazolium, pyrazolium, pyrrolidinium, piperidinium, tetraalkylammonium or tetraalkylphosphonium salt.

Ionic liquids for use in the present invention include salts (preferably halide salts, and especially chloride salts) of imidazoles, pyridines, pyridazines, pyrazines, oxazoles, triazoles or pyrazoles. Preferred ionic liquids for use in the present invention are imidazolium, pyridinium, pyridazinium, pyrazinium, oxazolium, triazolium or pyrazolium halide salts.

Especially preferred ionic liquids are halide salts of an alkylated or polyalkylated compound of pyridine, pyridazine, pyrimidine, pyrazine, imidazole, pyrazole, oxazole or triazole.

Also preferred ionic liquids for use in the present invention are those comprising an imidazolium, pyridinium, pyridazinium, pyrazinium, oxazolium, triazolium, pyrazolium, pyrrolidinium or piperidinium halide salt, with imidazolium halide salts (particularly chloride) being particularly preferred.

Thus, ionic liquids suitable for use in the present invention include those selected from a compound of formula:

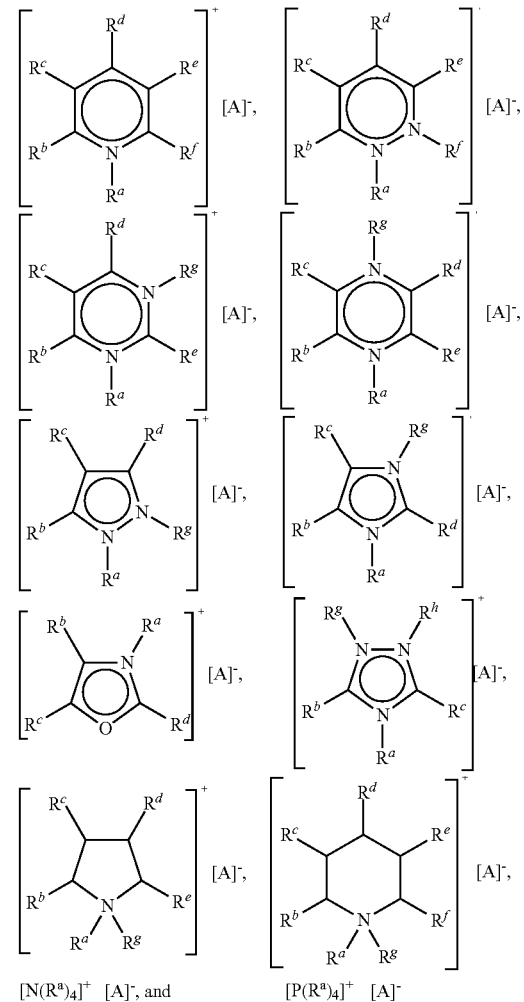

wherein
each $R^a$ is independently selected from a $C_1$ to $C_{40}$ linear or branched alkyl or a $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, $C_1$ to $C_{30}$ aralkyl and $C_1$ to $C_{30}$ alkaryl;
each $R^b$, $R^c$, $R^d$, $R^e$, $R^f$, $R^g$ and $R^h$ can be the same or different and are each independently selected from H or any of the $R^a$ groups as defined above; and
$[A]^-$ represents a monovalent anion (halide is preferred, and chloride is especially preferred).

Also preferred are ionic liquids selected from a compound of formula:

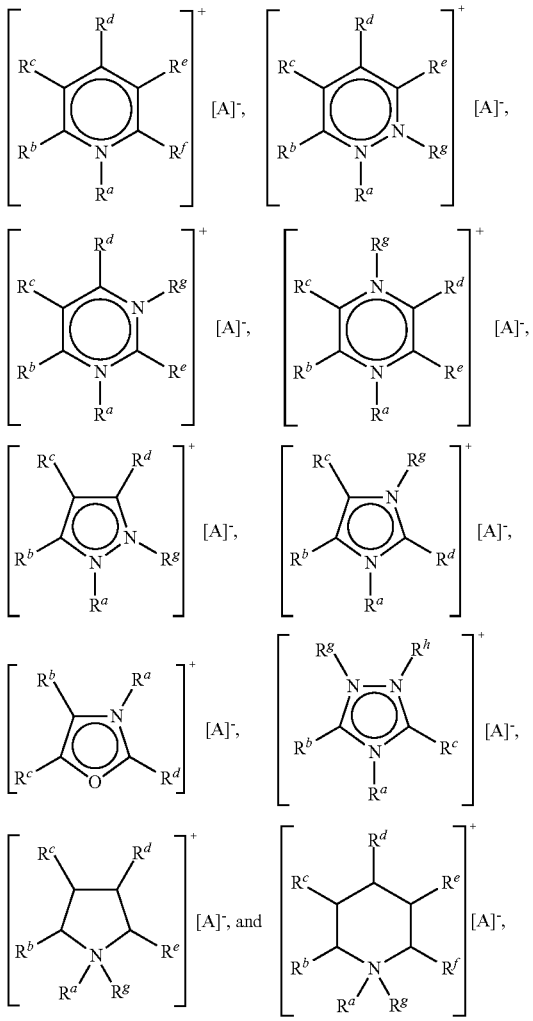

wherein $R^a$-$R^h$ and $[A]^-$ are as defined above.

Also preferred are ionic liquids selected from a compound of formula:

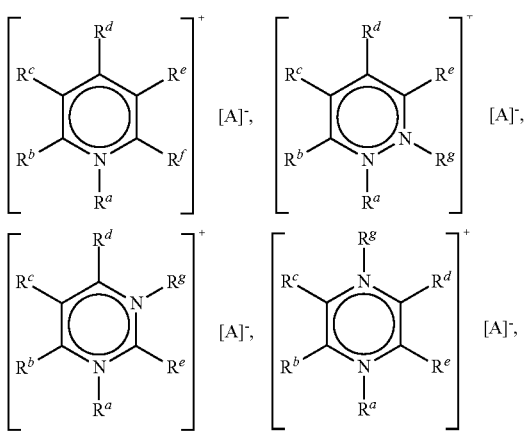

wherein $R^a$-$R^h$ and $[A]^-$ are as defined above.

Also preferred are ionic liquids selected from a compound of formula:

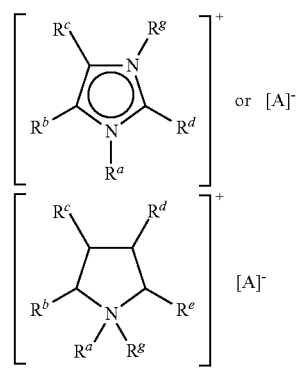

wherein $[A]^-$, $R^a$, $R^b$, $R^c$, $R^d$, $R^e$ and $R^g$ are as defined above.

Imidazole-based ionic liquids selected from a compound of formula:

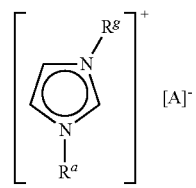

wherein $R^a$, $R^g$ and $[A]^-$ are as defined above are especially useful.

In the above formulae, it is preferred that each $R^a$ represents $C_1$ to $C_{40}$ (preferably $C_1$ to $C_{20}$, even more preferably $C_1$ to $C_8$) linear or branched alkyl.

Also, in the above formulae, it is preferred that each $R^g$ and $R^h$ represents $C_1$ to $C_{40}$ (preferably $C_1$ to $C_{20}$, more preferably $C_1$ to $C_8$) linear or branched alkyl.

Particularly preferred are ionic liquids of the above formulae wherein $R^b$, $R^c$, $R^d$, $R^e$, $R^f$, $R^g$ and $R^h$ each represents hydrogen.

A further preferred group of ionic liquids are those having the above formulae wherein $R^a$, $R^g$ and $R^h$ each represents a $C_1$-$C_{20}$ alkyl group.

The anion $[A]^-$ in the ionic liquids of the above formulae is preferably halide, i.e. $F^-$, $Cl^-$, $Br^-$ or $I^-$. $Cl^-$ or $Br^-$ are preferred halide anions, and $Cl^-$ is especially preferred.

Specific examples of suitable ionic liquids for the catalyst compositions of the present invention include:
1-butyl-3-methylimidazolium halide
1-octyl-3-methylimidazolium halide
1-decyl-3-methylimidazolium halide
1-dodecyl-3-methylimidazolium halide
1-ethyl-3-methylimidazolium halide
1-hexyl-3-methylimidazolium halide
1-hexylpyridinium halide
1-octylpyridinium halide In the above examples of suitable ionic liquids, it is preferred that the halide anion is chloride.

Good results have been obtained when 1-ethyl-3-methylimidazolium chloride or 1-butyl-3-methylimidazolium chloride are employed as starting materials for the catalyst compositions of the present invention.

With regards to the indium salt starting material of the catalyst composition of the present invention, indium(III) halides (i.e. $InF_3$, $InCl_3$, $InBr_3$ and $InI_3$). However, indium (III) chloride and indium(III) bromide are preferred, and indium(III) chloride is especially preferred.

The amount of free indium(III) chloride used to form the catalyst composition of the present invention is typically in the ratio of 1 mole % to 100 mole % (preferably 1 mole % to 50 mole %, more preferably 1 mole % to 30 mole %, even more preferably 1 mole % to 10 mole %) of the starting materials (e.g. organic ionic liquid). Good results have been obtained using amount ranges of 2 mole % to 7 mole % and 3 mole % to 6 mole %.

Typical ratio ranges of indium(III) chloride to organic ionic liquid vary from 4:1 to 1:1. Preferably the indium(III) chloride to organic ionic liquid ratio is from 3:1 to 2.5:1, and even more preferably, the ratio is 2:1 to 2.5 to 1. Good results have been obtained at an indium(III) chloride to organic ionic liquid ratio of 2:1.

According to a second aspect of the present invention, there is provided a process for the production of a catalyst composition as defined above, said process comprising admixing an organic ionic liquid as defined above with an indium(III) salt (preferably an indium(III) halide, even more preferably indium(III) chloride).

Preferably, the admixing is conducted at or beyond the melting point of the organic ionic liquid, typically at a temperature range of 25° C. to 200° C. (preferably 50° C. to 150° C., even more preferably 60° C. to 100° C.).

The catalyst composition of the present invention is preferably miscible with water. This has the advantage that the catalyst can be isolated after use by extraction with water.

Thus, for example, a catalyst composition for use in the process of the present invention can be formed from indium (III) chloride in conjunction with room temperature ionic liquid systems (RTILS) based e.g. on the 1,3-dialkylimidazolium ring system (or any other suitable organic cationic species) to yield a Lewis-acid catalyst system ("chloroindate melt"), which can be recovered from the alkylation/acylation reaction mixture by extraction with water and which, upon removal of water, yields the indium(III) chloride catalyst system, which may be recycled.

According to a third aspect of the present invention, there is provided a process for the Lewis acid catalysed electrophilic substitution of an aromatic substrate comprising the use of the catalyst composition according to the present invention.

Thus, the catalyst of the present invention is particularly effective in Lewis acid catalysed electrophilic substitution reactions (e.g. Friedel-Crafts alkylation and Friedel-Crafts acylation).

In accordance with the present invention, there is provided a process for the Friedel-Crafts alkylation or Friedel-Crafts acylation of an aromatic substrate comprising mixing the catalyst composition with an aromatic substrate and an alkylation or acylating agent.

It will be appreciated that these steps can be carried out in any suitable order. Preferably, the aromatic substrate is added to the catalyst composition, and the alkylating or acylating agent added subsequently, or the catalyst is added to the aromatic substrate followed by addition of the alkylating or acylating agent.

It is preferred that the catalyst composition is melted before the aromatic substrate is added.

After mixing the melted catalyst composition, the alkylating or acylating agent is added and the alkylation or acylation reaction is allowed to take place. The reaction temperature will depend on the nature of the substrate. However, typical temperature ranges for the alkylation and acylation reactions are 25° C. to 200° C., preferably 50° C. to 150° C. and more preferably 70° C. to 90° C.

After reaction, the alkylated or acylated aromatic product is isolated the reaction mixture by optionally adding a water-immiscible organic solvent to the reaction mixture to form an organic solution containing the product; and adding water to the reaction mixture in order to dissolve the catalyst composition. The immiscible solutions can then be separated into two components, namely the aqueous extracts containing the catalyst composition and the product or organic solution containing the product. The immiscible organic solvent can be removed from the product by distillation. The catalyst composition can be recovered by distillation/evaporation.

Any suitable water-immiscible solvent can be used to dissolve alkylated or acylated aromatic product. Typically used solvents include hexanes, diethyl ether, benzene, toluene and dichloromethane.

The alkylation and acylation processes of the present invention offers significant advantages compared to prior art processes because the catalyst can be recycled for subsequent reuse. Also the alkylation and acylation reactions can be conducted without the need for an additional reaction solvent (typically in Friedel-Crafts acylation reactions, nitrobenzene is employed as the reaction solvent). This reduces the amount of organic waste requiring disposal.

According to a fourth aspect of the present invention there is provided a process for the Friedel-Crafts alkylation of an aromatic substrate comprising reacting the aromatic substrate with an alkylation agent, in the presence of a catalyst composition as defined herein, to form an alkyl-substituted aromatic compound The alkylating agent is typically an alkyl halide, olefin or alcohol. Alternatively the alkylating agent is an alkyl halide substituent, an olefin substituent or an alcohol substituent, said substituent being attached to a ring carbon atom of the aromatic substrate such that the reaction results in an intramolecular alkylation reaction to form a fused ring, e.g:

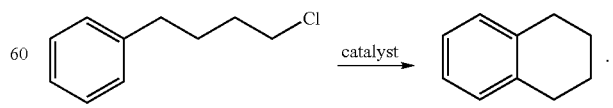

The alkylating agent typically comprises a linear or branched $C_1$ to $C_{20}$ alkyl halide; a linear or branched $C_2$ to $C_{20}$ olefin; or a linear or branched $C_1$ to $C_{20}$ alcohol; or a $C_3$ or $C_5$ alkyl halide substituent, a $C_4$ to $C_5$ olefin substituent or a $C_3$ to $C_5$ alcohol substituent, said substituent being attached to a ring carbon atom of the aromatic substrate such that the reaction results in an intramolecular alkylation reaction to form a fused ring.

Preferred alkylating agents are selected from a $C_1$ to $C_{20}$ alkyl halide or a $C_3$ to $C_5$ alkyl halide substituent, said substituent being attached to a ring carbon atom of the aromatic substrate such that the reaction results in an intramolecular alkylation reaction to form a fused ring.

Compounds containing an alkyl chloride or alkyl bromide group are especially preferred. Even more preferred are alkyl chloride alkylating agents.

According to a fifth aspect of the present invention there is provided a process for the Friedel-Crafts acylation of an aromatic substrate comprising reacting the aromatic substrate with an acylation agent, in the presence of a catalyst composition as defined herein, to form an aromatic ketone.

Any suitable acylating agent can be used. Preferably, the acylating agent is selected from: a cyclic aliphatic acid halide, a linear or branched aliphatic acid halide or an aromatic acid halide; a carboxylic acid; or a carboxylic acid anhydride. The acylating agent may also comprise a linear aliphatic acid halide substituent, a carboxylic acid substituent, or an acid anhydride substituent, said substituent being attached to a ring carbon atom of the aromatic substrate such that the reaction results in an intramolecular acylation reaction to form a fused ring, e.g.:

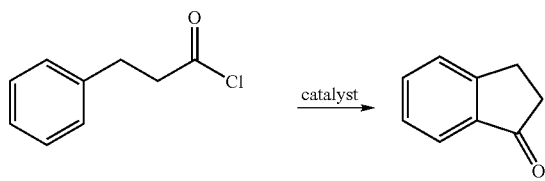

Also preferred are acylating agents comprising a $C_4$ to $C_{10}$ cyclic aliphatic acid halide, a $C_2$ to $C_{20}$ linear or branched aliphatic acid halide or a $C_7$ to $C_{20}$ aromatic acid halide; a $C_2$ to $C_{20}$ carboxylic acid; and a $C_4$ to $C_{20}$ acid anhydride; or the acylating agent is a $C_3$ to $C_5$ linear aliphatic acid halide substituent or a $C_3$ to $C_5$ carboxylic acid substituent said substituent being attached to a ring carbon atom of the aromatic substrate such that the reaction is an intramolecular acylation reaction to form a fused ring.

Especially preferred are acylating agents comprising a $C_2$ to $C_{20}$ linear or branched aliphatic acid halide; or a $C_3$ to $C_5$ linear aliphatic acid halide substituent said substituent being attached to a ring carbon atom of the aromatic substrate such that the reaction is an intramolecular acylation to form a fused ring.

Particularly preferred acylating agents include acid halides or the acylating agent can be an acid halide substituent present on the aromatic substrate. Acid chlorides or acid chloride substituents are especially preferred.

For example, acylating agents useful in the process of the present invention include compounds of the general formulae $$R^1COX \quad (I)$$

and $$R^1CO(O)COR^2 \quad (II),$$

wherein each $R^1$ and $R^2$, which may be the same or different, represents a substituted or unsubstituted aliphatic, aromatic or heterocyclic group containing from 1 to 40, preferably 1 to 25 or 1 to 10, and most preferably 1 to 8 carbon atoms, and X represents a leaving group, such as halide (preferably chloride or bromide).

Thus, for example, each of $R^1$ and $R^2$ may be the same or different and each is independently selected from:

$C_1$ to $C_{40}$ straight chain or branched alkyl which may be substituted by one to three groups selected from: $C_1$ to $C_6$ alkoxy, $C_6$ to $C_{10}$ aryl, $NO_2$, $C_1$ to $C_{30}$ aralkyl and $C_1$ to $C_{30}$ alkaryl; and $C_3$ to $C_8$ cycloalkyl wherein said alkyl or cycloalkyl group may be substituted with 1-3 substituents independently selected from: $C_1$ to $C_{10}$ alkyl, $C_3$ to $C_8$ cycloalkyl, or $OR^3$ wherein $R^3$ is selected from $C_1$ to $C_{20}$ alkyl.

Specific examples of acylating agents include: acetic anhydride, propanoic anhydride, isobutyric anhydride, trifluoroacetic anhydride, monochloroacetyl anhydride, dichloroacetyl anhydride, acetyl chloride, monochloroacetyl chloride, dichloroacetyl chloride, propanoyl chloride, isobutanoyl chloride, pivaloyl chloride, and crotonyl chloride. Particularly useful are acylating agents include acetic anhydride, propanoic anhydride, isobutyric anhydride, acetyl chloride, propanoyl chloride and butanoyl chloride.

The present process has been successfully employed for e.g. the Friedel-Crafts acylation of an aromatic substrate with an acylation agent to form a ketone, wherein a system of indium (III) chloride and a 1,3-dialkylated imidazolium chloride or other organic anionic species is used.

Thus, the present invention includes a homogeneous process for the Friedel-Crafts acylation of various aromatic substrates, which comprises using a combination of indium(III) chloride and a 1,3-dialkylated imidazolium chloride or other organic cationic species, whereby the amount of free indium (III) chloride used is in the ratio of 1 mole % to 100 mole % of the starting materials, and where the product can be removed easily from the reaction mixture by a simple extraction of the catalyst system from the reaction mixture with water, and wherein the indium based catalyst system can be regenerated by subsequent removal of water from the aqueous wash, and wherein the recovered indium based catalyst system may be re-employed in the conversion of fresh starting materials with no significant large loss in conversion of starting materials to products.

It will be noted that the alkylation and acylation processes employing the catalyst of the present invention are of general applicability to a wide range of substrates and wide range of alkylation/acylation reagents. These include substrates that comprise at least one aromatic group. The aromatic group may be substituted with various substituents. Providing that these substituents are stable under the Friedel-Crafts reaction conditions, or have been suitably protected (see e.g. Greene, T. W. Protective Groups in Organic Synthesis, Wiley, New York, 1981), the present processes may be used successfully on such substrates.

Typical starting materials for the acylation reaction include one or more of the following: toluene, anisole, benzoic anhydride, benzoyl chloride, acetic anhydride and acetyl chloride.

As indicated above, in the alkylation and acylation process of the present invention, the product may be removed from the reaction mixture by a simple extraction of the catalyst system from the reaction mixture with water. The product can be removed as a liquid (e.g. by decantation) or solid (e.g. by decantation, filtration, etc.) directly from the reaction mixture or can be dissolved in a water-immiscible organic solvent and separated from the catalyst component of the reaction mixture by extraction. The organic solvent containing dissolved product can be removed by distillation.

Advantageously, the indium based catalyst system can be separated from the reaction mixture as an aqueous solution. The catalyst can then be regenerated by subsequent removal of water from the aqueous phase. Also, it has been surprisingly found that it is possible to reuse the regenerated catalyst directly after removal of the water without the need for any further purification steps, although if necessary further purification steps may be carried out in order to optimize the catalyst purity/efficiency.

Unless otherwise indicated, the terms used herein have the following meanings:

"Alkyl" (including alkyl portions of alkyoxy, alkaryl, aralkyl, alkylamino, dialkylamino) represents straight and branched carbon chains containing from 1 to 40 carbon atoms, preferably 1 to 20 carbon atoms and more preferably 1 to 8 carbon atoms.

"Cycloalkyl" represents saturated carbocyclic rings branched or unbranched containing from 3 to 20 carbon atoms, preferably 3 to 8 carbon atoms. Such cycloalkyl groups include cyclopentyl and cyclohexyl.

"Heterocycloalkyl" represents a saturated, branched or unbranched carbocyclic ring containing from 3 to 12 carbon atoms, preferably from 4 to 6 carbon atoms, wherein the carbocyclic ring is interrupted by 1 to 3 heteroatom moieties selected from —O—, or —N($C_1$ to $C_6$ alkyl), or NH. Such heterocycloalkyl groups include 2- or 3-tetrahydrofuranyl, 2-, 3- or 4-piperidinyl, 2-, 3- or 4-piperizinyl, morpholinyl, 2- or 3-pyrrolidinyl and 2- or 4-dioxanyl.

"Aryl" including aryl moieties in e.g. aralkyl represents a carbocyclic group containing from 6 to 15 carbon atoms (preferably from 6 to 10 carbon atoms) and having at least one aromatic ring, with all available substitutable carbon atoms of the carbocyclic group being intended as possible points of attachment. Preferred aryl groups include phenyl and naphthyl.

"Heteroaryl" represents cyclic groups having at least one heteroatom selected from —O— or —N—, said heteroatom interrupting a carbocyclic ring structure and having a sufficient number of delocalised pi electrons to provide aromatic character, with the aromatic heterocyclic groups preferably containing from 2 to 14 carbon atoms. Suitable heteroaryl groups include pyridine, indole, imidazole, pyridazine, pyrazine, oxazole, triazole, pyrazole, and purines and pyrimidines.

The basic reaction involved in the acylation process of the invention is shown in the following equation:

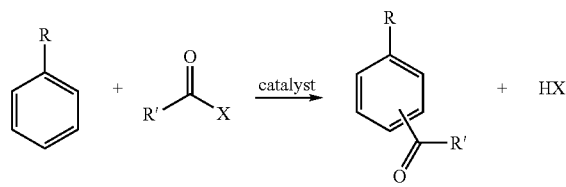

wherein R and R' can represent any suitable substituent. Examples of suitable aromatic substrates include toluene and anisole. Examples of suitable acylating agents include benzoic anhydride, benzoyl chloride, acetic anhydride and acetyl chloride, all of which are all readily available.

The starting materials for the catalyst composition e.g. indium(III) halides and ethylmethylimidazolium chloride and butylmethylimidazolium chloride are also readily available.

In an illustrative practical operation of the acylation reaction of the present invention, indium(III) chloride and the 1,3-dialkylimidazolium system (e.g. 1,3-dialkylimidazolium chloride) are stirred together at 80° C. until a melt is formed. This melt is the catalyst composition of the present invention. The nature of the reaction taking place between the organic ionic liquid, 1,3-dialkylimidazolium chloride and indium(III) chloride is uncertain. However, it is believed that the composition may contain $[bmim]^+ In_2Cl_7^-$. Other ionic species {including $[bmim]^+ In_xCl_y^-$ wherein x and y are integers from 1 to 10) may also be present in the composition.

The aromatic substrate (e.g. anisole or toluene) is added, followed by the acylating agent (such as acetic anhydride or benzoic anhydride).

The mixture is then stirred at a temperature of 80° C., for a period of time (typically 2 hours), after which time the reaction mixture is removed from the source of heat. A water-immiscible solvent may then be added. This solvent may be unrelated to the starting materials of the reaction, or it may be related (e.g. the water-immiscible solvent may be the same as the aromatic substrate—i.e. excess starting material such as anisole or toluene may be added at this stage, since they are water-immiscible The indium based catalyst system of the present invention may then be removed from the reaction by washing the solvent solution with water.

The aqueous solution can then be dehydrated in vacuo to remove water, followed by drying (e.g. in vacuo), to yield the recycled indium based catalyst system, which may then be re-employed as a catalyst with fresh starting materials.

The desired product of the acylation reaction (the ketone) may be liberated from the solvent solution by washing this with either hot water, or with aqueous sodium hydroxide solution to remove the benzoic acid (produced in benzoylation reactions using benzoic anhydride) and any excess acylating agent (such as acetyl chloride or benzoic anhydride).

Finally, distillation of the resulting mixture yields unreacted aromatic substrate which can be fed back into the process, and the ketone product.

The processes of the present invention may be conducted as a batch process or advantageously, as a continuous process.

Selectivity

The selectivity achieved using the acylation process of the present invention to benzoylate anisole has been found to be the same obtained for any other processes were used for comparison (an para:ortho isomer ratio of ca. 94% was achieved).

Recyclability

In the benzoylation of anisole with benzoic anhydride, the amount of free indium(III) chloride used (as a component of the chloroindate melt) was 5 mole % of the anisole used in the reaction.

The reaction was carried out at 80° C. for two hours in every case. Diethyl ether was used as the water-immiscible solvent, and the indium based catalyst system was removed from the reaction mixture by aqueous washing followed by dehydration. The chloroindate melt thus obtained was re-used in the conversion of fresh starting materials to products. The process was repeated until 6 runs had been carried out.

Conversion of starting materials based on anisole started at 79% and surprisingly remained at 62% after the sixth run.

In all cases, the isomer selectivity remained at ca. 94%.

The present invention will be illustrated further by way of the following examples and figures:

FIG. 1 is a schematic diagram showing the process steps for the acylation of anisole with benzoic anhydride using a catalyst composition of the present invention.

EXAMPLE 1

1-Butyl-3-methylimidazolium chloride (1.0 g) (5.65 mmol) was added to indium(III) chloride (2.5 g) (11.3 mmol) and stirred together at 80° C. until the mixture formed an opaque white liquid (10 min).

Anisole (10 ml, 9.95 g, 91.9 mmol) was added, and the mixture stirred for 5 min. Benzoic anhydride (23 g, 101.7 mmol, 1.1 equivalents based on anisole) was then added to the reaction mixture, and the mixture stirred under a closed atmosphere at 80° C. for 2 hr.

The yield of 4-methoxybenzophenone based on anisole was 79.9% (HPLC).

The reaction mixture was then removed from the source of heat, and when it had cooled to ambient temperature, diethyl ether (100 ml) was added, and the mixture shaken until everything had dissolved to form a homogenous solution.

This solution was then shaken with water (3×30 ml), and the aqueous extracts were combined, and then concentrated in vacuo. Finally, the residue was heated to ca. 100° C. under vacuum to remove residual water whereupon it resembled in appearance the opaque white liquid previously described.

This liquid was then taken and re-used as a catalyst for the conversion of fresh anisole and benzoic anhydride as described above.

The ether extract was washed with 2M sodium hydroxide (solution) (2×70 ml) yielding and finally water (50 ml), and the solvents removed in vacuo to yield the product, a mixture of 2-methoxybenzophenone and 4-methoxybenzophenone.

The process is further illustrated in FIG. 1. In FIG. 1, anisole and benzoic anhydride are fed into a batch reactor containing the chloroindate melt. The mixture is stirred at 80° C. for several hours.

The reaction mixture is run into a separation chamber. Here organic solvent is added (unnecessary if the reaction was run anisole rich—i.e. a large excess of anisole is employed). The chloroindate melt is extracted by washing repeatedly with water.

The chloroindate melt solution is evaporated to dryness, and is fed back into step 1.

Benzoic acid and benzoic anhydride are removed by washing with NaOH (or hot water) leaving 4-methoxybenzophenone.

Distillation yields the product, as well as anisole, which can be re-used in Step 1.

EXAMPLE 2

1-Butyl-3-methylimidazolium chloride (1.0 g) (5.65 mmol) was added to indium(III) chloride (2.5 g) (11.3 mmol) and stirred together at 80° C. until the mixture formed an opaque white liquid (10 min).

Toluene (0.6 ml, 0.52 g, 5.67 mmol) was added followed by benzoic anhydride (1.4 g, 6.19 mmol, 1.1 equivalents with respect to toluene).

The mixture was stirred at 100° C. and left to stir overnight. HPLC analysis indicated that the reaction had gone to completion.

Diethyl ether (20 ml) was added, and the mixture washed with water (3×20 ml).

The aqueous extracts were combined and dried as previously described to yield chloroindate melt which was re-used in conversion of starting materials under the same conditions.

Again, full conversion of the starting materials was observed.

The invention claimed is:

1. A catalyst composition formed by combining an organic ionic liquid with an indium(III) halide, wherein the ionic liquid comprises a pyridazinium, pyrazinium, pyrimidinium, oxazolium, triazolium, pyrrolidinium or a piperidinium salt, wherein the pyrrolidinum or piperidinium salt selected from the following formula:

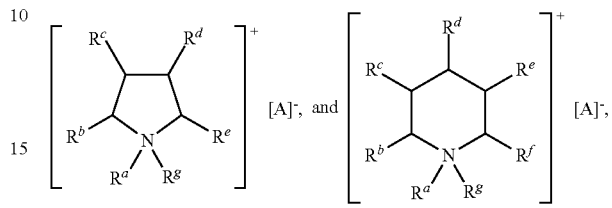

wherein $R^a$ and $R^g$ are independently selected from a $C_1$ to $C_{40}$ linear or branched alkyl or a $C_3$ to $C_8$ cycloalkyl group, wherein said alkyl or cycloalkyl group is substituted by one to three groups selected from $C_1$ to $C_6$ alkoxy, $C_6$ to $C_{10}$ aryl, $C_1$ to $C_{30}$ aralkyl and $C_1$ to $C_{30}$ alkaryl;

wherein each $R^b$, $R^c$, $R^d$, $R^e$ and $R^f$ can be the same or different and are each independently selected from H or any of the $R^a$ groups as defined above; and

[A]⁻ represents a halide anion.

2. A catalyst composition comprising in admixture (a) an organic ionic liquid and (b) an indium(III) halide, wherein the ionic liquid comprises a pyridazinium, pyrazinium, pyrimidinium, oxazolium, triazolium, pyrrolidinium or a piperidinium salt, wherein the pyrrolidinum or piperidinium salt selected from the following formula:

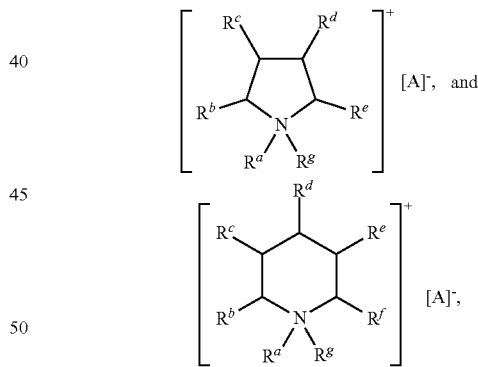

wherein $R^a$ and $R^g$ are independently selected from a $C_1$ to $C_{40}$ linear or branched alkyl or a $C_3$ to $C_8$ cycloalkyl group, wherein said alkyl or cycloalkyl group is substituted by one to three groups selected from $C_1$ to $C_6$ alkoxy, $C_6$ to $C_{10}$ aryl, $C_1$ to $C_{30}$ aralkyl and $C_1$ to $C_{30}$ alkaryl;

wherein each $R^b$, $R^c$, $R^d$, $R^e$ and $R^f$ can be the same or different and are each independently selected from H or any of the $R^a$ groups as defined above; and

[A]⁻ represents a halide anion.

3. A catalyst composition according to claim 1 where the catalyst composition comprises ionic species resulting from reaction between the organic ionic liquid and indium chloride.

4. A catalyst composition comprising a plurality of ionic species including:
   (a) cationic species derived from an organic ionic liquid, and
   (b) at least one species comprising indium, wherein the ionic liquid comprises a pyridazinium, pyrazinium, pyrimidinium, oxazolium, triazolium, pyrrolidinium or a piperidinium salt, wherein the pyrrolidinum or piperidinium salt selected from the following formula:

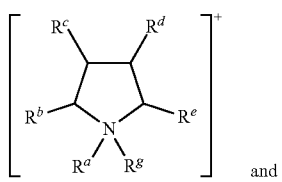

and

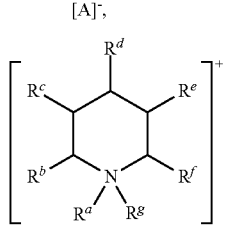

wherein $R^a$ and $R^g$ are independently selected from a $C_1$ to $C_{40}$ linear or branched alkyl or a $C_3$ to $C_8$ cycloalkyl group, wherein said alkyl or cycloalkyl group is substituted by one to three groups selected from $C_1$ to $C_6$ alkoxy, $C_6$ to $C_{10}$ aryl, $C_1$ to $C_{30}$ aralkyl and $C_1$ to $C_{30}$ alkaryl;

wherein each $R^b$, $R^c$, $R^d$, $R^e$ and $R^f$ can be the same or different and are each independently selected from H or any of the $R^a$ groups as defined above; and

[A]⁻ represents a halide anion.

5. A catalyst composition according to claim 4 further comprising a halide ion.

6. A catalyst composition according to claim 4 wherein the indium(III) salt is an indium(III) halide.

7. A catalyst composition according to claim 1 wherein the ionic liquid is a halide salt of an alkylated or polyalkylated compound of pyridazine, pyrimidine, pyrazine, oxazole or triazole.

8. A catalyst composition according to claim 1 wherein the ionic liquid is selected from a compound of formula:

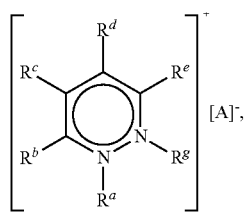 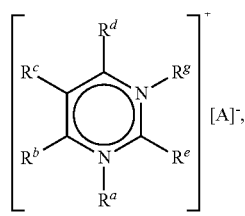

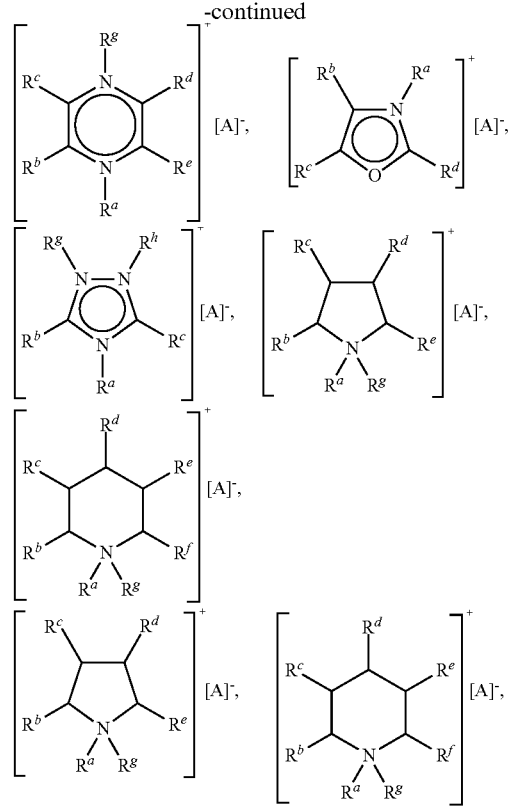

wherein
each $R^a$ is independently selected from a $C_1$ to $C_{40}$ linear or branched alkyl or a $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, $C_1$ to $C_{30}$ aralkyl and $C_1$ to $C_{30}$ alkaryl;
each $R^b$, $R^c$, $R^d$, $R^e$, $R^f$, $R^g$ and $R^h$ can be the same or different and are each independently selected from H or any of the $R^a$ groups as defined above, except in the case of pyrrolidiniun or piperidinium wherein $R^g$ can not be hydrogen; and
[A]⁻ represents a halide anion.

9. A catalyst composition according to claim 1 wherein the ionic liquid is a compound of formula:

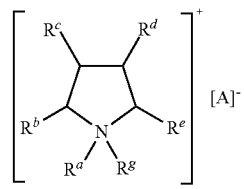

wherein each $R^a$ and $R^g$ is independently selected from a $C_1$ to $C_{40}$ linear or branched alkyl or a $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, $C_1$ to $C_{30}$ aralkyl and $C_1$ to $C_{30}$ alkaryl;
each $R^b$, $R^c$, $R^d$ and $R^e$ can be the same or different and are each independently selected from H or any of the $R^a$ groups as defined above; and
[A]⁻ represents a halide anion.

10. A catalyst composition according to claim 8 wherein each $R^a$ represents $C_1$ to $C_{40}$ linear or branched alkyl.

11. A catalyst composition according to claim 8 wherein each $R^g$ and $R^h$ represents $C_1$ to $C_{40}$ linear or branched alkyl.

12. A catalyst composition according to claim 8 wherein $R^b$, $R^c$, $R^d$, $R^e$, $R^f$, $R^g$ and $R^h$ each represents hydrogen, except in the case of pyrrolidiniun or piperidinium wherein $R^g$ can not be hydrogen.

13. A catalyst composition according to claim 8 wherein $[A]^-$ represents $Cl^-$ or $Br^-$.

14. A catalyst composition according to claim 1 wherein the indium(III) halide is indium(III) chloride.

15. A process for the production of a catalyst composition according to claim 1, said process comprising admixing an organic ionic liquid with an indium(III) halide, wherein the ionic liquid is selected from a compound of formula:

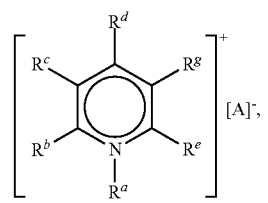

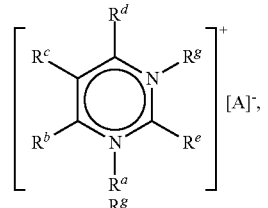

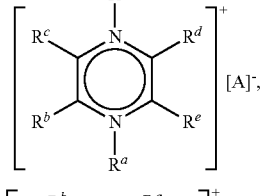

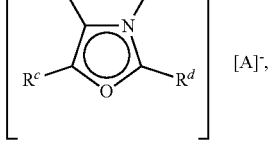

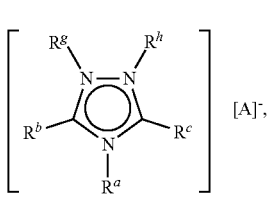

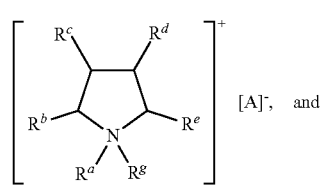

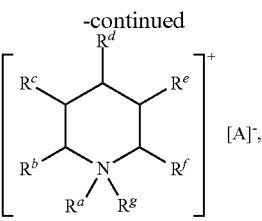

wherein
each $R^a$ is independently selected from a $C_1$ to $C_{40}$ linear or branched alkyl or a $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, $C_1$ to $C_{30}$ aralkyl and $C_1$ to $C_{30}$ alkaryl;
each $R^b$, $R^c$, $R^d$, $R^e$, $R^f$, $R^g$ and $R^h$ can be the same or different and are each independently selected from H or any of the $R^a$ groups as defined above, except in the case of pyrrolidiniun or piperidinium wherein $R^g$ can not be hydrogen; and
$[A]^-$ represents a halide anion.

16. A process for the Lewis acid catalysed electrophilic substitution of an aromatic substrate comprising the use, as a catalyst, of a composition according to claim 1.

17. A process according to claim 16 wherein the Lewis acid catalysed electrophilic substitution reaction is a Friedel-Crafts alkylation reaction to form an alkyl substituted aromatic compound, or Friedel-Crafts acylation reaction to form an aromatic ketone.

18. A process according to claim 16 comprising admixing a catalyst composition formed by combining an organic ionic liquid with an indium(III) halide, with an aromatic substrate and an alkylating or acylating agent.

19. A process according to claim 16 wherein the product is isolated from the reaction mixture by a procedure comprising the steps of:
(i) optionally adding a water-immiscible organic solvent to form an organic solution containing the product; and
(ii) adding water to the reaction mixture to dissolve the catalyst composition and separating the aqueous extracts containing the catalyst composition from the product or from the organic solution containing the product; and
(iii) removing any solvent from the product.

20. A process according to claim 16 further comprising recycling the catalyst for subsequent use.

21. A process according to claim 16 wherein the catalyst is isolated by evaporation of water.

22. A process according to claim 18 wherein the alkylating agent is an alkyl halide, olefin or alcohol; or wherein the alkylating agent is an alkyl halide substituent, an olefin substituent or an alcohol substituent, said substituent being attached to a ring carbon atom of the aromatic substrate such that the reaction results in an intramolecular alkylation reaction to form a fused ring.

23. A process according to claim 18 wherein the alkylating agent is a linear or branched $C_1$ to $C_{20}$ alkyl halide; a linear or branched $C_2$ to $C_{20}$ olefin; or a linear or branched $C_1$ to $C_{20}$ alcohol; or a $C_3$ or $C_5$ alkyl halide substituent, a $C_4$ to $C_5$ olefin substituent or a $C_3$ to $C_5$ alcohol substituent, said substituent being attached to a ring carbon atom of the aromatic substrate such that the reaction results in an intramolecular alkylation reaction to form a fused ring.

24. A process according to claim 18 wherein the alkylating agent is a $C_1$ to $C_{20}$ alkyl halide or a $C_3$ to $C_5$ alkyl halide substituent, said substituent being attached to a ring carbon atom of the aromatic substrate such that the reaction results in an intramolecular alkylation reaction to form a fused ring.

25. A process according to claim 22 wherein the alkyl halide or alkyl chloride substituent is an alkyl chloride or alkyl bromide.

26. A process according to claim 18 wherein the acylating agent is selected from: a cyclic aliphatic acid halide, a linear or branched aliphatic acid halide or an aromatic acid halide; a carboxylic acid; or a carboxylic acid anhydride; or wherein the acylating agent is a linear aliphatic acid halide substituent, a carboxylic acid substituent, or an acid anhydride substituent, said substituent being attached to a ring carbon atom of the aromatic substrate such that the reaction results in an intramolecular acylation reaction to form a fused ring.

27. A process according to claim 18 wherein the acylating agent is selected from: a $C_4$ to $C_{10}$ cyclic aliphatic acid halide, a $C_2$ to $C_{20}$ linear or branched aliphatic acid halide or a $C_7$ to $C_{20}$ aromatic acid halide; a $C_2$ to $C_{20}$ carboxylic acid; and a $C_4$ to $C_{20}$ acid anhydride; or wherein the acylating agent is a $C_3$ to $C_5$ linear aliphatic acid halide substituent or a $C_3$ to $C_5$ carboxylic acid substituent, said substituent being attached to a ring carbon atom of the aromatic substrate such that the reaction is an intramolecular acylation reaction to form a fused ring.

28. A process according to claim 18 wherein the acylating agent is a $C_2$ to $C_{20}$ linear or branched aliphatic acid halide; or a $C_3$ to $C_5$ linear aliphatic acid halide substituent said substituent being attached to a ring carbon atom of the aromatic substrate such that the reaction is an intramolecular acylation to form a fused ring.

29. A process according to claim 26 wherein the acid halide or acid halide substituent is an acid chloride or acid bromide.

30. A process according to claim 18 wherein the acylating agent is selected from acetic anhydride, propanoic anhydride, isobutyric anhydride, acetyl chloride, propanoyl chloride and butanoyl chloride.

31. A process according to claim 18 for the Friedel-Crafts acylation of an aromatic substrate with an acylation agent to form a ketone, wherein a system of indium (III) chloride and a 1,3 dialkylated imidazolium chloride or other organic anionic species is used.

32. A process according to claim 18 wherein the alkylation or acylation product is removed from the reaction mixture by a simple extraction of the catalyst system from the reaction mixture with water.

33. A process according to claim 18 wherein the indium based catalyst system is regenerated by subsequent removal of water from the aqueous wash.

34. A process according to claim 18 wherein the starting materials for the reaction include one or more of the following: toluene, anisole, benzoic anhydride, benzoyl chloride, acetic anhydride and acetyl chloride.

35. An acylation process as claimed in claim 16 claims wherein the ionic liquid is an imidazolium chloride selected from ethylmethylimidazolium chloride or butylmethylimidazolium chloride.

36. A process according to claim 18 wherein the reaction product is liberated from the solvent solution by washing with hot water or with an aqueous sodium hydroxide solution.

37. Use of a system of indium (III) chloride and a 1,3-dialkylated imidazolium chloride or other organic cationic species in a Friedel-Crafts acylation reaction.

* * * * *